(12) United States Patent
Wood

(10) Patent No.: US 7,612,222 B2
(45) Date of Patent: Nov. 3, 2009

(54) METHOD FOR THE REDISTRIBUTION OF POLYORGANOSILOXANES

(75) Inventor: Larry Herbert Wood, Campbellsburg, KY (US)

(73) Assignee: Dow Corning Corporation, Midland, MI (US)

( * ) Notice: Subject to any disclaimer, the term of this patent is extended or adjusted under 35 U.S.C. 154(b) by 42 days.

(21) Appl. No.: 11/885,298

(22) PCT Filed: Mar. 15, 2006

(86) PCT No.: PCT/US2006/009252

§ 371 (c)(1),
(2), (4) Date: Aug. 29, 2007

(87) PCT Pub. No.: WO2006/124106

PCT Pub. Date: Nov. 23, 2006

(65) Prior Publication Data

US 2008/0146751 A1 Jun. 19, 2008

Related U.S. Application Data

(60) Provisional application No. 60/681,317, filed on May 16, 2005.

(51) Int. Cl.
C07F 7/02 (2006.01)
C07F 7/21 (2006.01)
C08G 77/08 (2006.01)

(52) U.S. Cl. .......................... 556/460; 556/450; 528/12

(58) Field of Classification Search .................. 525/477
See application file for complete search history.

(56) References Cited

U.S. PATENT DOCUMENTS

| | | | |
|---|---|---|---|
| 2,673,843 A * | 3/1954 | Humphrey et al. | 521/47.5 |
| 4,073,801 A | 2/1978 | Moretto et al. | |
| 4,113,760 A | 9/1978 | Frey et al. | |
| 4,177,201 A * | 12/1979 | de Montigny et al. | 556/416 |
| 4,276,425 A * | 6/1981 | Burkhardt et al. | 556/460 |
| 4,329,483 A * | 5/1982 | Speier | 556/436 |
| 4,423,240 A * | 12/1983 | Yeboah | 556/460 |
| 5,068,383 A | 11/1991 | Bourgoin et al. | |
| 5,194,553 A | 3/1993 | Freeburne et al. | |
| 5,196,559 A | 3/1993 | Schulz, Jr. et al. | |
| 5,233,070 A | 8/1993 | Bokerman et al. | |
| 5,247,116 A | 9/1993 | Buese et al. | |
| 5,420,325 A * | 5/1995 | Razzano | 556/460 |
| 5,473,037 A * | 12/1995 | Itoh et al. | 528/12 |
| 5,783,718 A * | 7/1998 | Doguet et al. | 556/453 |
| 5,965,683 A | 10/1999 | Nye et al. | |
| 6,040,410 A * | 3/2000 | Schneider et al. | 528/14 |
| 6,136,996 A | 10/2000 | Rubinsztajn et al. | |
| 6,316,655 B1 * | 11/2001 | Hall et al. | 556/450 |
| 6,326,452 B1 * | 12/2001 | Berrier et al. | 528/12 |
| 6,737,495 B2 | 5/2004 | Bordone et al. | |

FOREIGN PATENT DOCUMENTS

| | | |
|---|---|---|
| EP | 0569230 | 11/1993 |
| EP | 0484959 | 8/1997 |
| EP | 0604112 | 9/1997 |
| EP | 0779316 | 4/2005 |

* cited by examiner

*Primary Examiner*—Randy Gulakowski
*Assistant Examiner*—Robert Loewe
(74) *Attorney, Agent, or Firm*—Matthew T. Fewkes

(57) ABSTRACT

Linear hydroxy endblocked linear polyorganosiloxanes, linear chloro-endblocked polyorganosiloxanes, and mixtures thereof, are redistributed in a process by contacting the linear polyorganosiloxanes, with a diorganodichlorosilane having the formula $R'_2SiCl_2$, wherein R' is an alkyl group containing 1-8 carbon atoms; in the presence of an aqueous hydrochloric acid catalyst; to form a redistributed mixture containing cyclic polyorganosiloxanes and chloro-endblocked polyorganosiloxanes. The process generates less amounts of undesired branched siloxane species than processes which utilize an alumina catalyst.

8 Claims, No Drawings

METHOD FOR THE REDISTRIBUTION OF POLYORGANOSILOXANES

CROSS REFERENCE TO RELATED APPLICATIONS

This application is a U.S. national stage filing under 35 U.S.C. §371 of PCT Application No. PCT/US2006/009252 filed on 15 Mar. 2006, currently pending, which claims the benefit of U.S. Provisional Patent Application No. 60/681,317 filed 16 May 2005 under 35 U.S.C. §119 (e). PCT Application No. PCT/US2006/009252 and U.S. Provisional Patent Application No. 60/681,317 are hereby incorporated by reference.

FIELD OF THE INVENTION

This invention is directed to a process for the redistribution of high molecular weight linear hydroxy endblocked polyorganosiloxanes, high molecular weight linear chloro-endblocked polyorganosiloxanes, or mixtures thereof, with diorganodichlorosilanes to produce cyclic polyorganosiloxanes and chloro-endblocked polyorganosiloxanes of low molecular weight using aqueous hydrochloric acid as a catalyst. The reaction is promoted with good mixing to contact the two phases. The process has the advantage of generating less undesired branched siloxane species than a process which utilizes an alumina catalyst.

BACKGROUND OF THE INVENTION

Current industrial processes for the manufacture of silicone fluids, resins and rubbers typically require as starting materials either linear hydroxy endblocked polyorganosiloxanes or cyclic polyorganosiloxanes. These polysiloxanes can be produced by the hydrolysis of diorganodihalosilanes. This process results in a mixture of cyclic polyorganosiloxanes and linear hydroxy endblocked polyorganosiloxanes. Separation of this mixture to isolate a desired linear fraction or cyclic fraction results in an excess of linear materials or cyclic materials, as well as materials of undesired molecular weight. Therefore, a process which allows for converting the linear hydroxy endblocked polyorganosiloxanes and/or the linear chloro-endblocked polyorganosiloxanes to cyclic polyorganosiloxanes and that allows for adjusting the molecular weight of the polyorganosiloxane chains is desirable to allow recovery of these excess siloxanes.

Known methods for enhancing the production of cyclic polyorganosiloxanes include cracking of the linear hydroxy endblocked polyorganosiloxanes, which is capital intensive; vacuum hydrolysis, which has poor enhancement capabilities; and aqueous hydrolysis, which tends to sacrifice chloride recovery. Other methods for enhancing the production of cyclic polyorganosiloxanes require the addition of solvents and/or surfactants which makes recovery of the product more difficult and can compromise product purity. Other catalysts, such as alumina, generate undesired branched siloxane species such as $CH_3SiO_{3/2}$ through cleavage of organic groups from silicon.

The present process offers advantages over previously described processes as noted above. In addition, the present process can be used not only to enhance the production of cyclic polyorganosiloxanes, but also to control the cyclic polyorganosiloxane content from about zero to greater than 90 percent by weight of the product. The aqueous HCl catalyst used herein improves the rate of redistribution while minimizing organic cleavage. The linear hydroxy endblocked polyorganosiloxanes and/or the linear chloro-endblocked polyorganosiloxanes can easily be redistributed to more desirable cyclic polyorganosiloxanes, and chloride-end terminated polyorganosiloxanes typically having 2-8 siloxane units. In addition, no solvents or surfactants are required, and the aqueous HCl catalyst is readily available.

BRIEF SUMMARY OF THE INVENTION

The invention relates to a process for the redistribution of linear hydroxy endblocked polyorganosiloxanes and/or linear chloro-endblocked polyorganosiloxanes. The process is carried out by contacting a linear hydroxy endblocked polyorganosiloxane having Formula I:

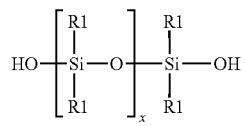

and/or a linear chloro-endblocked polyorganosiloxane having Formula II:

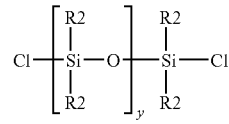

with a diorganodichlorosilane having the formula $R'_2SiCl_2$; in the presence of a catalyst which facilitates the redistribution of polyorganosiloxanes. The catalyst is aqueous hydrochloric acid and it is typically used in an amount of 0.1-70 percent by weight based on the weight of the linear hydroxy endblocked polyorganosiloxane and/or chloro-endblocked polyorganosiloxane and diorganodichlorosilane. The aqueous catalyst may contain saturated concentrations of HCl at the temperature and pressure conditions at which the redistribution is conducted. A redistributed mixture is formed containing cyclic polyorganosiloxanes and linear chloro-endblocked polyorganosiloxanes having Formula II.

In Formulas I and II, x and y have a value of 1-5,000; and R', R1, and R2 represent alkyl groups containing 1-8 carbon atoms. The alkyl group can be, for example, methyl, ethyl, propyl, isopropyl, n-butyl, isobutyl, tert-butyl, or sec- butyl. Most typically, the alkyl groups R', R1 and R2 will comprise the methyl group.

The preferred diorganodichlorosilane is dimethyldichlorosilane. The cyclic polyorganosiloxane in the redistributed mixture are typically cyclic polymers containing 3-8 silicon atoms. Chloro-endblocked polyorganosiloxanes in the redistributed mixture are predominately polymers having a degree of polymerization (DP) of 2-8. These and other features of the invention will become apparent from a consideration of the detailed description.

DETAILED DESCRIPTION OF THE INVENTION

According to the invention, linear hydroxy endblocked polyorganosiloxanes, linear chloro-endblocked polyorganosiloxanes, or mixtures thereof, are redistributed with a diorganodichlorosilane using aqueous hydrochloric acid as catalyst. The process results in the formation of cyclic polyorganosiloxanes and chloro-endblocked polyorganosiloxanes of low molecular weight, i.e., short chain length.

The linear hydroxy endblocked polyorganosiloxanes and the linear chloro-endblocked polyorganosiloxanes that are redistributed according to the method of the invention are polymers having Formulas I and II.

Diorganodichlorosilanes corresponding to the above formula $R'_2SiCl_2$ include, for example, compounds such as dimethyldichlorosilane $(CH_3)_2SiCl_2$, ethylmethyldichlorosilane $(CH_3)(C_2H_5)SiCl_2$, diethyldichlorosilane $(C_2H_5)_2SiCl_2$, di-n-propyldichlorosilane $(n-C_3H_7)_2SiCl_2$, di-i-propyldichlorosilane $(i-C_3H_7)_2SiCl_2$, hexylmethyldichlorosilane $(CH_3)(CH_3)(CH_2)_4(CH_2)SiCl_2$, di-n-butyldichlorosilane $(n-C_4H_9)_2SiCl_2$, di-i-butyldichlorosilane $(i-C_4H_9)_2SiCl_2$, di-t-butyldichlorosilane $(t-C_4H_9)_2SiCl_2$, and n-butylmethyldichlorosilane $CH_3(n-C_4H_9)SiCl_2$. The preferred diorganodichlorosilane is dimethyldichlorosilane (DMDCS).

The catalyst used herein comprises aqueous hydrochloric acid, which is typically used in the redistribution reaction in an amount of from 0.1-70 percent by weight, based on the weight of the linear hydroxy endblocked polyorganosiloxanes, the linear chloro-endblocked polyorganosiloxanes, or mixtures thereof, and the diorganodichlorosilanes used in the reaction. The aqueous catalyst may contain saturated concentrations of HCl at the temperature and pressure conditions at which the redistribution is conducted.

The cyclic polyorganosiloxanes formed as a result of the redistribution generally consist of mixtures of cyclic polyorganosiloxanes containing 3-8 silicon atoms including, for example, hexaalkylcyclotrisiloxanes such as hexamethylcyclotrisiloxane, octaalkylcyclotetrasiloxanes such as octamethylcyclotetrasiloxane, decaalkylcyclopentasiloxanes such as decamethylcyclopentasiloxane, dodecaalkylcyclohexasiloxanes such as dodecamethylcyclohexasiloxane, tetradecaalkylcycloheptasiloxanes such as tetradecamethylcycloheptasiloxane, and hexadecaalkylcyclooctasiloxanes such as hexadecamethylcyclooctasiloxane. The chloro-endblocked polyorganosiloxanes that are produced according to the redistribution method of the invention are polymers having Formula II. In one embodiment, a majority of these redistributed chloro-endblocked polyorganosiloxanes have a DP of 1-10, alternatively 2-8.

The linear hydroxy endblocked polyorganosiloxanes, linear chloro-endblocked polyorganosiloxanes, or mixtures thereof, and diorganodichlorosilanes are contacted with the aqueous HCl catalyst which facilitates their redistribution to a mixture of cyclic polyorganosiloxanes and chloro-endblocked polyorganosiloxanes of low molecular weight. Contact of the catalyst with the linear polyorganosiloxanes and the diorganodichlorosilanes can be affected by standard means for contacting liquids, for example, by a batch process or by a continuous-flow process. The process can be conducted in any standard reactor suitable for mixing corrosive materials.

The required contact time for the linear hydroxy endblocked polyorganosiloxanes, the linear chloro-endblocked polyorganosiloxanes, the mixtures thereof and the diorganodichlorosilanes with the catalyst to effect redistribution will depend upon such factors as temperature, type of linear polyorganosiloxanes and diorganodichlorosilanes, and concentration of the catalyst. In general, contact times up to 3 hours have been found useful. The preferred contact time is generally less than 30 minutes, most preferably less than 5 minutes. The process can be carried out at a temperature between 0-100° C., but it is preferably conducted at ambient or room temperature, i.e., 20-25° C. (68-77° F.).

The amount of the linear hydroxy endblocked polyorganosiloxanes and/or the linear chloro-endblocked polyorganosiloxanes and the amount of the diorganodichlorosilanes that can be used in the redistribution reaction is the volume ratio necessary to generate the desired molecular weight distribution of linear chloro-endblocked polyorganosiloxanes. The determination of such volume ratios is within the scope of knowledge of those skilled in the art.

EXAMPLES

The following examples are set forth in order to illustrate the invention in more detail. The method of analysis used in the examples was Gel Permeation Chromatography (GPC) and Gas Chromatography (GC). Since GC is not able to measure higher molecular weight peaks, siloxane species of higher molecular weight that were present in the samples analyzed, are not included in the analysis results. For that reason, the percents by weight Before and After do not total 100 percent. The Before analysis results show values obtained on the mixture before it was added to the Teflon vessel. The After analysis results show values obtained after adding the mixture to the Teflon vessel, pressurizing the vessel with HCl, agitating the vessel by hand-shaking, allowing the contents to sit, relieving the pressure, opening the vessel, and sampling the siloxane mixture.

In Tables 1-3, $D_3$ to $D_8$ represent cyclic siloxanes comprising, respectively, difunctional D units of the formula $[(CH_3)SiO]_{3-8}$. $D_3$ to $D_8$ are, respectively, hexamethylcyclotrisiloxane, octamethylcyclotetrasiloxane, decamethylcyclopentasiloxane, dodecamethylcyclohexasiloxane, tetradecamethylcycloheptasiloxane, and hexadecamethylcyclooctasiloxane. $CEB_2$ to $CEB_8$ represent chloro-endblocked polyorganosiloxanes having chain lengths of 2-8, respectively.

Example 1

A mixture was formed by mixing together 98 grain of a linear hydroxy endblocked polydimethylsiloxane and 140 gram of dimethyldichlorosilane $Me_2SiCl_2$. To a Teflon vessel was added 12.72 gram of 37 percent by weight aqueous hydrochloric acid, and 43.13 gram of the mixture of linear hydroxy endblocked polydimethylsiloxane and dimethyldichlorosilane. The vessel was sealed and pressurized to 100 psig with gaseous hydrogen chloride. The vessel was agitated by hand shaking for 5 minutes to achieve saturation concentrations of aqueous hydrochloric acid at these new conditions and facilitate contact between the two phases. The pressure was released and a sample of a chlorosilane/siloxane phase was removed and analyzed. GPC analysis showed that the siloxane chains were shortened. Analysis of the chlorosilane/siloxane mixture Before and After by GC is shown in Table 1.

TABLE 1

Redistribution of $Me_2SiCl_2$/Siloxane Mixture

| Sample Composition, Weight Percent | Before | After |
|---|---|---|
| $D_3$ | 0.14 | 0.08 |
| $D_4$ | 0.43 | 4.14 |
| $D_5$ | 0.30 | 1.00 |
| $D_6$ | 0.19 | 0.18 |
| $D_7$ | 0.10 | 0.04 |
| $D_8$ | 0.07 | 0.02 |
| $Me_2SiCl_2$ | 48.60 | 6.37 |
| $CEB_2$ | 0.25 | 9.88 |

TABLE 1-continued

Redistribution of $Me_2SiCl_2$/Siloxane Mixture

| Sample Composition, Weight Percent | Before | After |
|---|---|---|
| $CEB_3$ | 0.09 | 7.96 |
| $CEB_4$ | 0.07 | 4.64 |
| $CEB_5$ | 0.06 | 3.4 |
| $CEB_6$ | 0.07 | 3.08 |
| $CEB_7$ | 0.07 | 2.66 |
| $CEB_8$ | 0.11 | 2.43 |
| Branching (ppm) | 40.0 | 45.2 |

Example 2

A mixture was formed by mixing together 98 gram of a linear hydroxy endblocked polydimethylsiloxane and 140 gram of dimethyldichlorosilane $Me_2SiCl_2$. To a Teflon vessel was added 11.5 gram of 37 percent by weight aqueous hydrochloric acid and 58.18 gram of the mixture of linear hydroxy endblocked polydimethylsiloxane and dimethyldichlorosilane. The vessel was sealed and pressurized to 100 psig with gaseous hydrogen chloride. The vessel was agitated by hand shaking periodically for 30 minutes, to achieve saturation concentrations of aqueous hydrochloric acid at these new conditions and facilitate contact between the two phases. The pressure was released and a sample of a chlorosilane/siloxane phase was removed and analyzed. GPC analysis showed that the siloxane chains were shortened. Analysis of the chlorosilane/siloxane mixture Before and After by GC is shown in Table 2.

TABLE 2

Redistribution of $Me_2SiCl_2$/Siloxane Mixture

| Sample Composition, Weight Percent | Before | After |
|---|---|---|
| $D_3$ | 0.07 | 0.12 |
| $D_4$ | 0.90 | 1.94 |
| $D_5$ | 1.25 | 0.92 |
| $D_6$ | 0.78 | 0.22 |
| $D_7$ | 0.21 | 0.07 |
| $D_8$ | 0.11 | 0.04 |
| $Me_2SiCl_2$ | 43.98 | 12.58 |
| $CEB_2$ | 0.16 | 5.74 |
| $CEB_3$ | 0.11 | 6.68 |
| $CEB_4$ | 0.08 | 7.08 |
| $CEB_5$ | 0.10 | 7.08 |
| $CEB_6$ | 0.13 | 6.63 |
| $CEB_7$ | 0.17 | 5.99 |
| $CEB_8$ | 0.24 | 5.30 |
| Branching (ppm) | 38.7 | 43.4 |

Example 3

A mixture was formed by mixing together 103.61 gram of a hydroxy endblocked linear polydimethylsiloxane and 120.02 gram of dimethyldichlorosilane $Me_2SiCl_2$. To a Teflon vessel was added 10.37 gram of 37 percent by weight aqueous hydrochloric acid and 50.96 gram of the mixture of linear hydroxy endblocked polydimethylsiloxane and dimethyldichlorosilane. The vessel was sealed and pressurized to 100 psig with gaseous hydrogen chloride. The vessel was agitated by hand shaking initially to achieve saturation concentrations of aqueous hydrochloric acid at these new conditions, and facilitate contact between the two phases. The vessel was then allowed to sit for three hours. The pressure was released and a sample of a chlorosilane/siloxane phase was removed and analyzed. GPC analysis showed that the siloxane chains were shortened. Analysis of the chlorosilane/siloxane mixture Before and After by GC is shown in Table 3.

TABLE 3

Redistribution of $Me_2SiCl_2$/Siloxane Mixture

| Sample Composition, Weight Percent | Before | After |
|---|---|---|
| $D_3$ | 0.13 | 0.12 |
| $D_4$ | 0.43 | 1.99 |
| $D_5$ | 0.29 | 0.98 |
| $D_6$ | 0.15 | 0.31 |
| $D_7$ | 0.10 | 0.15 |
| $D_8$ | 0.09 | 0.11 |
| $Me_2SiCl_2$ | 45.45 | 3.08 |
| $CEB_2$ | 0.22 | 6.03 |
| $CEB_3$ | 0.08 | 11.03 |
| $CEB_4$ | 0.05 | 12.18 |
| $CEB_5$ | 0.04 | 11.26 |
| $CEB_6$ | 0.03 | 9.66 |
| $CEB_7$ | 0.05 | 7.93 |
| $CEB_8$ | 0.05 | 6.35 |
| Branching (ppm) | 37 | 39 |

In Tables 1-3, the apparent increase in branching is due to the loss of chloride mass from the mixture of the linear hydroxy endblocked polydimethylsiloxane and the dimethyldichlorosilane due to hydrolysis of the dimethyldichlorosilane.

Other variations may be made in compounds, compositions, and methods described herein without departing from the essential features of the invention. The embodiments of the invention specifically illustrated herein are exemplary only and not intended as limitations on their scope except as defined in the appended claims.

I claim:

1. A process for the redistribution of linear hydroxy endblocked polyorganosiloxanes, linear chloro-endblocked polyorganosiloxanes, and mixtures thereof, comprising:

contacting (i) a linear hydroxy endblocked polyorganosiloxane having Formula I:

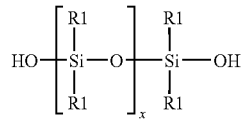

(ii) a chloro-endblocked polyorganosiloxane having Formula II:

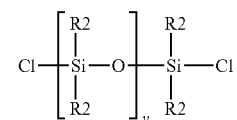

or (iii) a mixture of (i) and (ii)

with (iv) a diorganodichlorosilane having the formula $R'_2SiCl_2$ in the presence of a catalyst to form a redistributed mixture comprising cyclic polyorganosiloxanes and chloro-endblocked polyorganosiloxanes having Formula II;

wherein x and y represent integers having a value of 1-5,000 and R', R1, and R2 represent alkyl groups containing 1-8 carbon atoms;

and wherein the catalyst comprises aqueous hydrochloric acid and it is present in an amount of 0.1-70 percent by weight based on the weight of the linear hydroxy endblocked polyorganosiloxanes, the linear chloro-endblocked polyorganosiloxanes, and the diorganodichlorosilanes; and the aqueous HCl catalyst contains saturated concentrations of HCl at the temperature and pressure conditions at which the redistribution is conducted.

2. The process according to claim 1 wherein the diorganodichlorosilane is selected from the group consisting of dimethyldichlorosilane, ethylmethyldichlorosilane, diethyldichlorosilane, di-n-propyldichlorosilane, di-i-propyldichlorosilane, hexylmethyldichlorosilane, di-n-butyldichlorosilane, di-i-butyldichlorosilane, di-t-butyldichlorosilane, and n-butylmethyldichlorosilane.

3. The process according to claim 2 wherein the diorganodichlorosilane is dimethyldichlorosilane.

4. The process according to claim 1 wherein the cyclic polyorganosiloxane in the redistributed mixture are selected from the group consisting of hexamethylcyclotrisiloxane, octamethylcyclotetrasiloxane, decamethylcyclopentasiloxane, dodecamethylcyclohexasiloxane, tetradecamethylcycloheptasiloxane, and hexadecamethylcyclooctasiloxane.

5. The process according to claim 1 wherein the linear chloro-endblocked polyorganosiloxanes in the redistributed mixture comprise predominantly polymers wherein the degree of polymerization is 2-8.

6. The process according to claim 1 wherein the process is carried out at a temperature of 20-25° C.

7. The process according to claim 1 wherein the contact time for the linear hydroxy endblocked polyorganosiloxanes, linear chloro-endblocked polyorganosiloxanes, or mixtures thereof, and diorganodichlorosilanes with the catalyst to effect redistribution is less than 3 hours.

8. The process according to claim 7 wherein the contact time is less than 30 minutes.

* * * * *